US010568573B2

United States Patent
Campbell et al.

(10) Patent No.: US 10,568,573 B2
(45) Date of Patent: Feb. 25, 2020

(54) MITIGATION OF HEAD-MOUNTED-DISPLAY IMPACT VIA BIOMETRIC SENSORS AND LANGUAGE PROCESSING

(71) Applicant: Sony Interactive Entertainment LLC, San Mateo, CA (US)

(72) Inventors: Kevin Campbell, San Mateo, CA (US); Milan Cvetkovic, Los Angeles, CA (US); Patricio Garza, Los Angeles, CA (US); Abinadi Johnson, Los Angeles, CA (US); John Corenbaum, Los Angeles, CA (US); Quan Lau, Los Angeles, CA (US)

(73) Assignee: SONY INTERACTIVE ENTERTAINMENT LLC, San Mateo, CA (US)

( * ) Notice: Subject to any disclaimer, the term of this patent is extended or adjusted under 35 U.S.C. 154(b) by 77 days.

(21) Appl. No.: 15/452,354

(22) Filed: Mar. 7, 2017

(65) Prior Publication Data
US 2018/0256115 A1 Sep. 13, 2018

(51) Int. Cl.
*A61B 5/00* (2006.01)
*A61B 3/14* (2006.01)
(Continued)

(52) U.S. Cl.
CPC ............ *A61B 5/6803* (2013.01); *A61B 3/113* (2013.01); *A61B 3/14* (2013.01); *A61B 5/7405* (2013.01);
(Continued)

(58) Field of Classification Search
CPC ......... A61B 5/742; A61B 5/0015; A61B 5/01; A61B 5/0533; A61B 5/443; A61B 5/6803;
(Continued)

(56) References Cited

U.S. PATENT DOCUMENTS

2006/0224046 A1* 10/2006 Ramadas ............. A61B 5/0002
600/300
2007/0299362 A1* 12/2007 Epley ................... A61B 5/4863
600/559
(Continued)

FOREIGN PATENT DOCUMENTS

WO   WO 2018/165307   9/2018

OTHER PUBLICATIONS

PCT Application No. PCT/US2018/021353 International Search Report and Written Opinion dated May 8, 2018.
(Continued)

*Primary Examiner* — Carl H Layno
*Assistant Examiner* — Michael J Lau
(74) *Attorney, Agent, or Firm* — Polsinelli LLP

(57) ABSTRACT

Users of head-mounted displays (HMDs) often experience nausea and other symptoms often referred to a "virtual reality sickness." Various health and biometric sensors are employed to gather baseline sensor measurements. The HMD or a device associated with it can then generate a range or threshold such that any future sensor measurements that fall outside of the range or cross the threshold suggest a health concern for the user of the HMD. The HMD can also be coupled to a microphone, and natural language processing (NLP) is employed to detect negative words or noises made by the user that could also suggest a health concern for the user. After detecting the health concern, the HMD can warn its user, can shut off certain functions, can communicate with an external device, or can trigger an alarm.

18 Claims, 6 Drawing Sheets

(51) Int. Cl.
  *A61B 3/113* (2006.01)
  *A61B 5/053* (2006.01)
  *G09G 5/00* (2006.01)

(52) U.S. Cl.
  CPC ............ *A61B 5/0533* (2013.01); *G09G 5/003* (2013.01); *G09G 2370/04* (2013.01); *G09G 2370/16* (2013.01)

(58) Field of Classification Search
  CPC ......... A61B 5/7405; A61B 3/113; A61B 3/14; G09G 5/003; G09G 2370/04; G09G 2370/16; G02B 17/017
  USPC ....... 600/300; D14/372, 496, 432, 371, 125, D14/126, 129, 299; D16/300–342; 351/158, 153, 144; 345/7–9; 455/344
  See application file for complete search history.

(56) References Cited

U.S. PATENT DOCUMENTS

| | | | | |
|---|---|---|---|---|
| 2011/0184248 A1* | 7/2011 | Furuta | ................ | A61B 5/0002 600/300 |
| 2012/0050044 A1* | 3/2012 | Border | ................ | A61M 21/02 340/573.1 |
| 2013/0145482 A1* | 6/2013 | Ricci | ................ | H04W 4/90 726/28 |
| 2013/0278631 A1* | 10/2013 | Border | ................ | G02B 27/017 345/633 |
| 2013/0288777 A1* | 10/2013 | Short | ................ | A61B 5/16 463/23 |
| 2014/0121559 A1* | 5/2014 | Stevens | ................ | A61B 5/16 600/558 |
| 2015/0093729 A1* | 4/2015 | Plans | ................ | G06F 16/683 434/236 |
| 2015/0164418 A1* | 6/2015 | Johnson | ................ | A61B 5/4884 434/236 |
| 2015/0212647 A1* | 7/2015 | Kim | ................ | G02B 27/017 345/173 |
| 2015/0223731 A1* | 8/2015 | Sahin | ................ | A61B 5/16 600/301 |
| 2015/0326570 A1* | 11/2015 | Publicover | ................ | G06F 21/64 726/4 |
| 2016/0113517 A1* | 4/2016 | Lee | ................ | G01J 5/0859 600/474 |
| 2016/0131912 A1* | 5/2016 | Border | ................ | G02B 27/0176 345/8 |
| 2016/0167672 A1* | 6/2016 | Krueger | ................ | H04N 13/366 340/576 |
| 2016/0228771 A1* | 8/2016 | Watson | ................ | G06F 3/013 |
| 2016/0360970 A1* | 12/2016 | Tzvieli | ................ | G01J 5/0265 |
| 2017/0007165 A1* | 1/2017 | Jain | ................ | A61B 5/0478 |

OTHER PUBLICATIONS

PCT/US18/021353, Mitigation of Head-Mounted-Display Impact Via Biometric Sensors and Language Procesessings, Mar. 9, 2018.

* cited by examiner

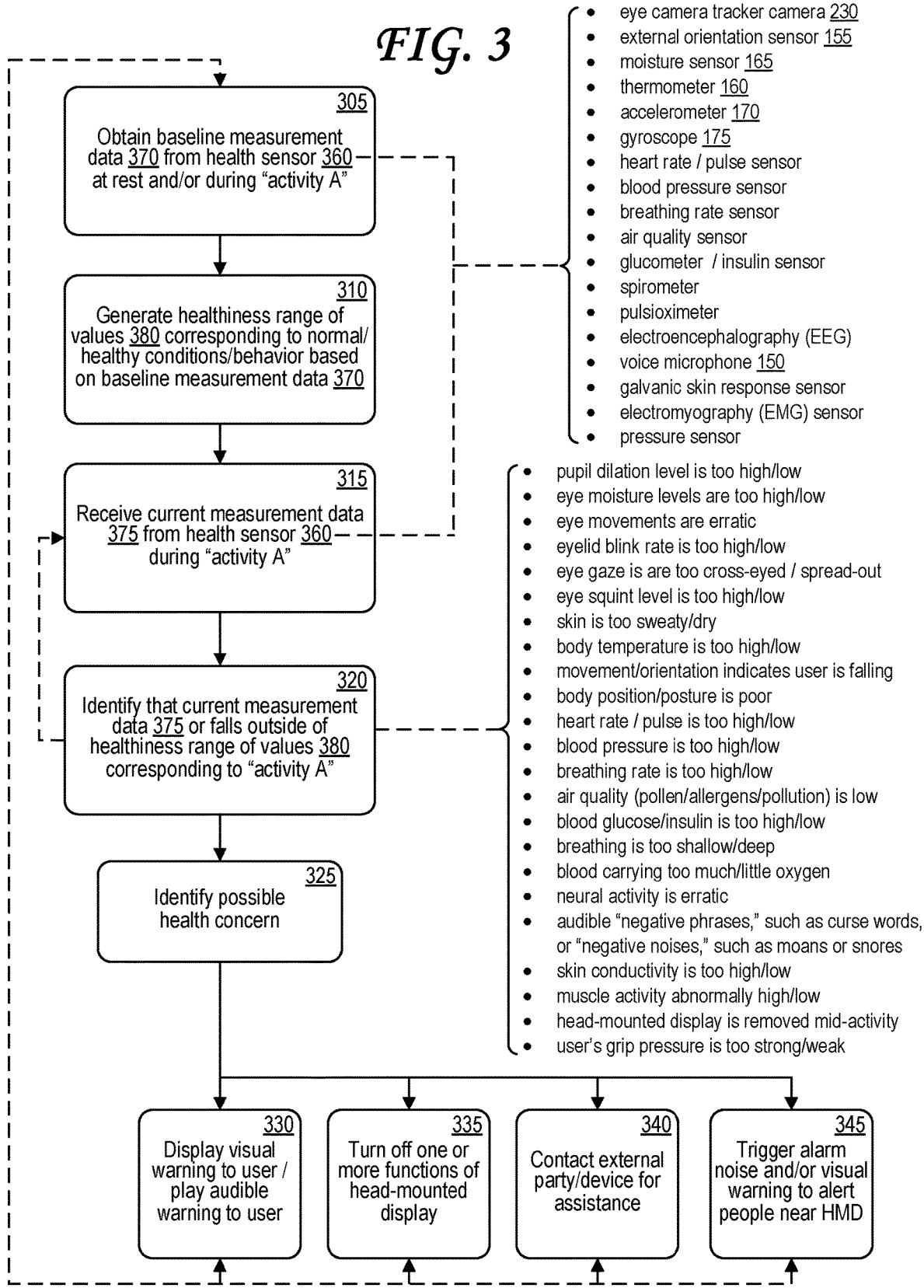

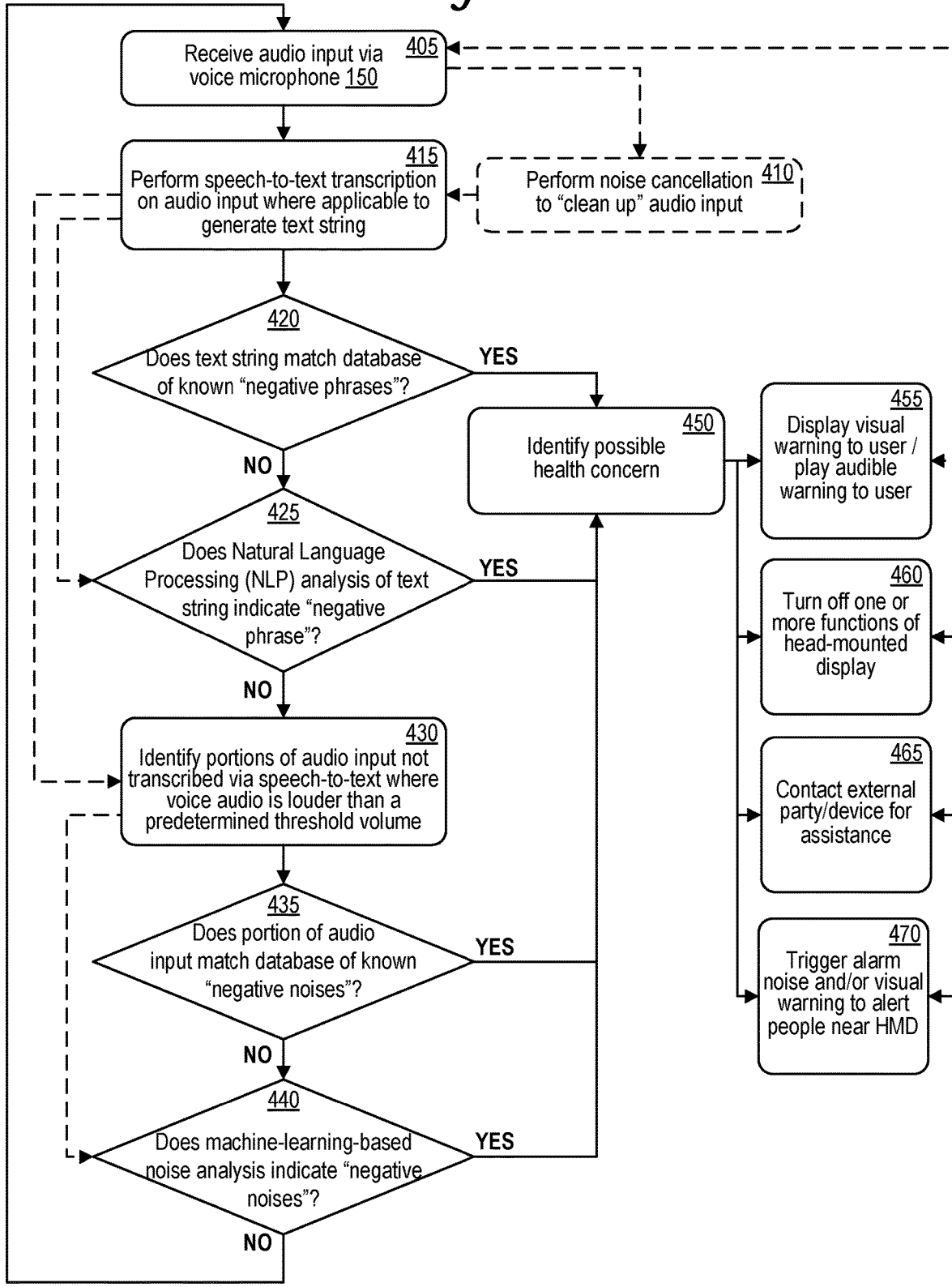

MITIGATION OF HEAD-MOUNTED-DISPLAY IMPACT VIA BIOMETRIC SENSORS AND LANGUAGE PROCESSING

BACKGROUND

1. Field of the Invention

The present invention generally concerns head-mounted display technologies. More particularly, the present invention concerns mitigation of ill health effects on users of head-mounted displays based on biometric sensor measurements and natural language processing.

2. Description of the Related Art

Head-mounted displays (HMDs) are displays typically integrated into glasses, goggles, helmets, or visors. A HMD typically includes a display directly visible to one or both eyes of a user wearing the head-mounted display. HMDs refer to both "augmented reality headsets," which typically include displays that are transparent or semi-transparent, and "virtual reality headsets," which typically block light from the outside world.

Motion sickness is typically caused by a "mismatch" between a person's visual system and the person's inner ear vestibular system. In particular, motion sickness is typically triggered when the person's visual system tells the brain that the body is stationary, but the person's inner ear vestibular system tells the brain the body is in motion.

Some users of HMDs experience nausea or other symptoms similar to those associated with motion sickness. This is sometimes referred to as "virtual reality sickness" or "VR sickness." Like motion sickness, virtual reality sickness is believed to be caused by a mismatch between a person's visual system and the person's inner ear vestibular system. In the case of virtual reality sickness, the person's inner ear vestibular system tells the brain the body is stationary, but the person's visual system tells the brain that the body is in motion.

Notably, several companies that presented virtual reality headsets at the January 2017 Consumer Electronics Show (CES) handed out nausea/vomit bags to event attendees hoping to try their products. Thus, there is a need for technologies mitigating the impact of head-mounted displays.

SUMMARY OF THE PRESENTLY CLAIMED INVENTION

A first claimed embodiment of the present invention involves a method for mitigation for a head-mounted display (HMD). The method includes receiving a baseline sensor measurement value from a health sensor, the health sensor having gathered the baseline sensor measurement value from a user of the head-mounted display (HMD). The method also includes generating a health threshold value based on the baseline sensor measurement. The method also includes receiving an active sensor measurement value from the health sensor, the health sensor having gathered the active sensor measurement value from the user of the head-mounted display (HMD) following generation of the health threshold value, and identifying that the active sensor measurement value has reached or crossed the health threshold value. The method also includes identifying a health concern associated with the user of the head-mounted display (HMD).

A second claimed embodiment of the present invention concerns a head-mounted display (HMD) system that includes body to be worn on the head a user and a display integrated with the body. The HMD system also includes a memory to store instructions and a processor coupled to the memory, wherein execution of the instructions by the processor causes the HMD system to perform a number of system operations. The system operations include receiving a baseline sensor measurement value from a health sensor, the health sensor having gathered the baseline sensor measurement value from the user. The system operations also include generating a health threshold value based on the baseline sensor measurement. The system operations also include receiving an active sensor measurement value from the health sensor, the health sensor having gathered the active sensor measurement value from the user following generation of the health threshold value and identifying that the active sensor measurement value has reached or crossed the health threshold value. The system operations also include identifying a health concern associated with the user.

A third-claimed embodiment of the present invention concerns a non-transitory computer readable storage medium having embodied thereon a program, wherein the program is executable by a processor to perform a program method of illness mitigation for a head-mounted display (HMD). The program method includes receiving a baseline sensor measurement value from a health sensor, the health sensor having gathered the baseline sensor measurement value from a user of the head-mounted display (HMD). The program method also includes generating a health threshold value based on the baseline sensor measurement. The program method also includes receiving an active sensor measurement value from the health sensor, the health sensor having gathered the active sensor measurement value from the user of the head-mounted display (HMD) following generation of the health threshold value, and identifying that the active sensor measurement value has reached or crossed the health threshold value. The program method also includes identifying a health concern associated with the user of the head-mounted display (HMD).

BRIEF DESCRIPTION OF THE DRAWINGS

FIG. 3 is a flow diagram illustrating a process for identifying possible concerns based on health sensor measurements.

FIG. 4 is a flow diagram illustrating a process for identifying possible concerns based on language processing.

DETAILED DESCRIPTION

Users of head-mounted displays (HMDs) often experience nausea and other symptoms often referred to a "virtual reality sickness." Various health and biometric sensors are employed to gather baseline sensor measurements. The HMD or a device associated with it can then generate a range or threshold such that any future sensor measurements that fall outside of the range or cross the threshold suggest a health concern for the user of the HMD. The HMD can also be coupled to a microphone, and natural language processing (NLP) is employed to detect negative words or noises made by the user that could also suggest a health concern for the user. After detecting the health concern, the HMD can warn its user, can shut off certain functions, can communicate with an external device, or can trigger an alarm.

Figure 1A:
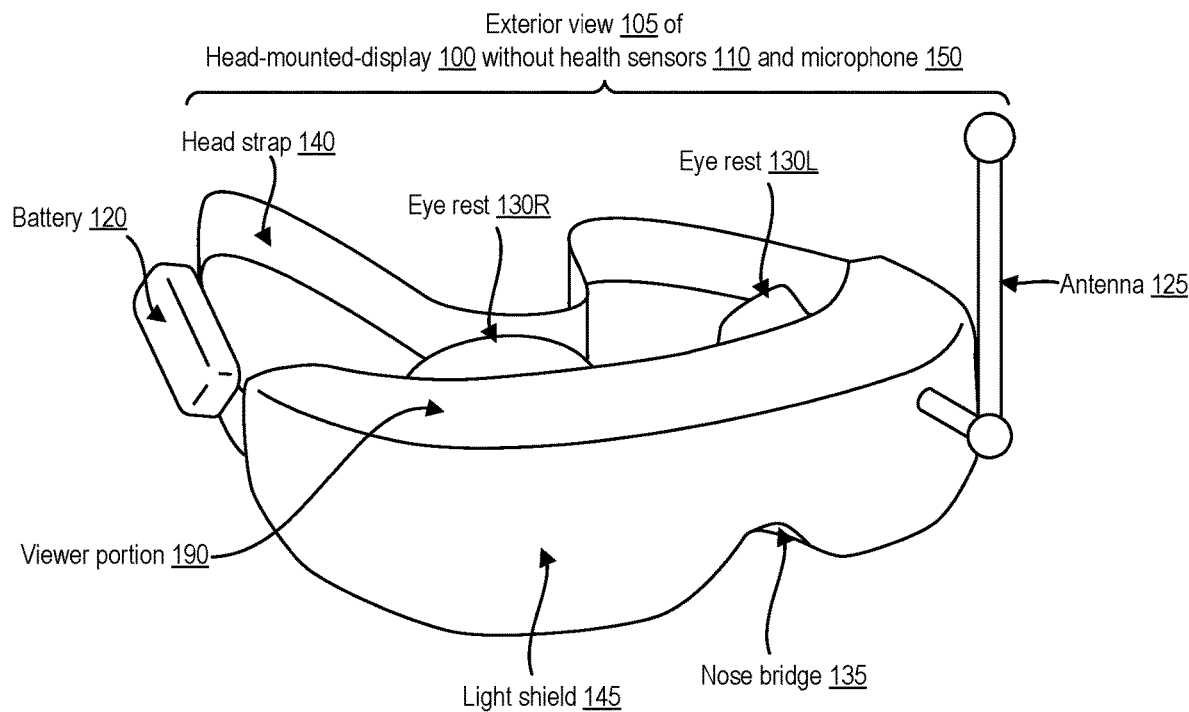
FIG. 1A illustrates an exterior view of a head-mounted display without health sensors and without a voice microphone.

FIG. 1A illustrates an exterior view 105 of a head-mounted display 100 without health sensors 110 and without a voice microphone 150.

The head-mounted display (HMD) 100 of FIG. 1A takes the form of body in the shape of a pair of "visor goggles" featuring a viewer portion 190 of the body with two eye rests 130 (130L and 130R) and a nose bridge 135, each of which help the HMD rest in place on a user's head. The two eye rests 130 (130L and 130R) may also serve to block light from reaching the user's eyes, particularly if the HMD 100 is a virtual reality headset. The viewer portion 190 is coupled to a head strap 140 that also helps keep the HMD 100 in place on the user's head. It should be understood that the HMD 100 discussed herein can omit or move at least some of these features and instead take on alternate body structures or form factors, such as that of a helmet, a pair of "swim" goggles, a pair of glasses, a headband, a blindfold, a monocle, an eyepatch, or a contact lens. The HMD 100 body may also include or be coupled to additional structures, such as a top strap going over the top of the head of the user, or a chin strap going underneath the chin of the user.

The HMD 100 includes an opaque or reflective light shield 145 around the exterior of the viewer portion 190. The light shield 145 blocks light from reaching a user's eyes during use of the HMD 100, allowing the user to be immersed in the virtual reality displayed by the HMD 100. That is to say, the HMD 100 is illustrated as a virtual reality headset rather than an augmented reality headset. It should be understood that the HMD 100 discussed herein can alternately omit the opaque/reflective light shield 145 and instead have at least a portion of the exterior of the viewer portion 190 near the user's eyes be at least partially transparent, translucent, or semitransparent. Such an omission of the light shield 145 can be used alongside a transparent, translucent, or semitransparent display technology, such as a projector-based display or organic light emitting diode (OLED) film display, to make the HMD 100 an augmented reality headset rather than a virtual reality headset. An augmented reality headset may also include opaque displays alongside transparent, translucent, or semitransparent areas. Regardless of whether the HMD 100 is a virtual reality headset or an augmented reality headset, it should be understood that the HMD 100 can use any display system 670 technology discussed herein with respect to FIG. 6, optionally paired with various types of lenses, reflectors, refractors, polarizers, diffusers, or some combination thereof.

The HMD 100 is also illustrated having a battery 120 coupled to the head strap 140. The battery 120 could alternately be located anywhere else in or along the body of the HMD 100, such as inside the viewer portion 190. The HMD 100 can alternately or additionally include another power source, such as a solar panel device, a wireless charging device, or an outlet for plugging into a wall socket.

The HMD 100 is also illustrated having an antenna 125. This is one example of a wireless communication interface used by the HMD 100. The wireless communication interface(s) of the HMD 100 may be used to communicate with one or more health sensors 110 and/or one or more microphones 150. The wireless communication interface(s) of the HMD 100 may be used to communicate with devices that the user of the HMD 100 is controlling or simply receiving visual data and/or audio data from, such as an unmanned aerial vehicle (UAV), a manned aerial vehicle, an unmanned ground vehicle (UGV), a manned ground vehicle, an unmanned (aquatic) surface vehicle (USV), a manned surface vehicle, an unmanned underwater vehicle (UUV), a manned underwater vehicle, an unmanned spacecraft, a manned spacecraft, a local device 510, a remote device 520, or any type of computer system 600.

The HMD 100 may include various types of wireless communication interfaces, including one or more receivers, transmitters, transceivers, or some combination thereof. The HMD 100 may include local wireless communication interfaces, such as communication interfaces for Bluetooth™, Bluetooth™ low energy, Bluetooth™ smart, radio waves, microwaves, infrared, visible light communication (VLC), ultraviolet, infrasonic, audible sound, ultrasonic, or some combination thereof. The HMD 100 may also include wireless communication interfaces for 802.11 Wi-Fi, 3G cellular, 4G cellular, or Long-Term-Evolution (LTE) cellular networks.

Figure 6:
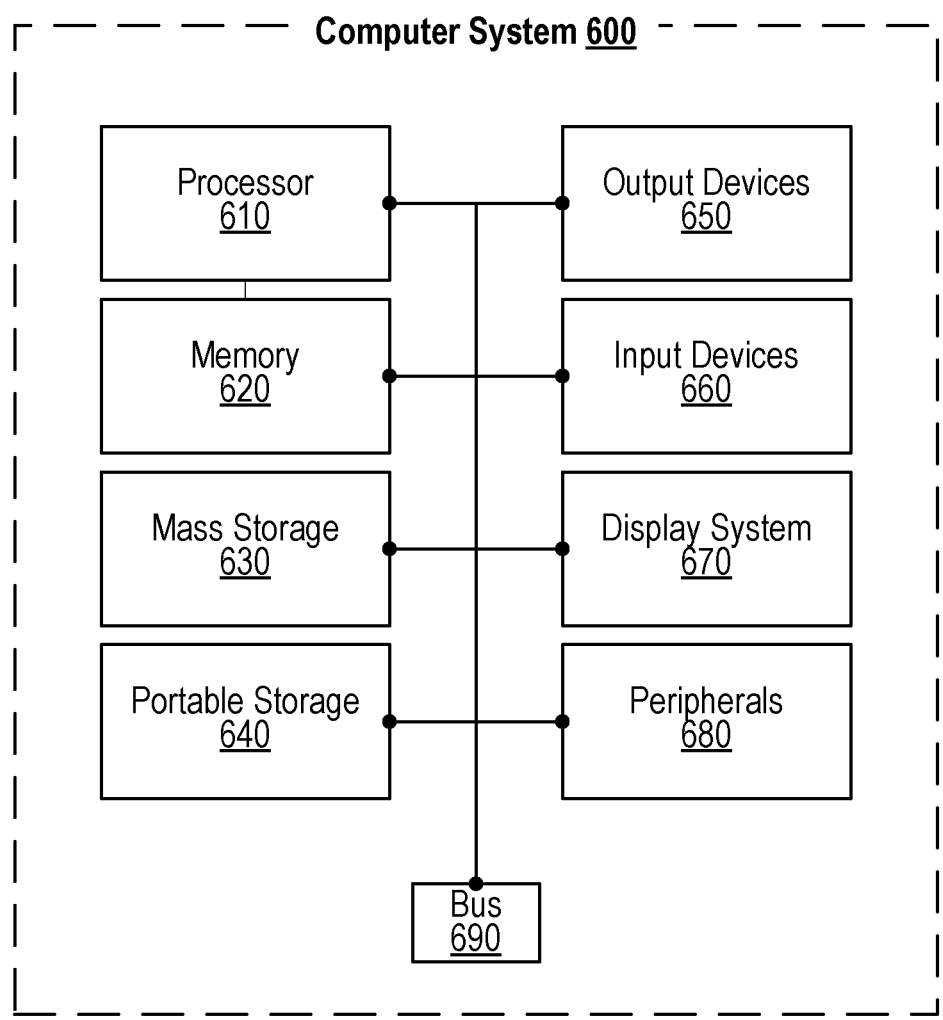
FIG. 6 is a block diagram of an exemplary computing device that may be used to implement an embodiment of the present invention.

The HMD 100 may include one or more computer systems 600, or may include at least a subset of any the computer system components illustrated in FIG. 6 or discussed with respect to FIG. 6. For example, the HMD 100 illustrated in FIG. 1A may include such components in the viewer portion 190 of the body of the HMD 100.

Figure 1B:
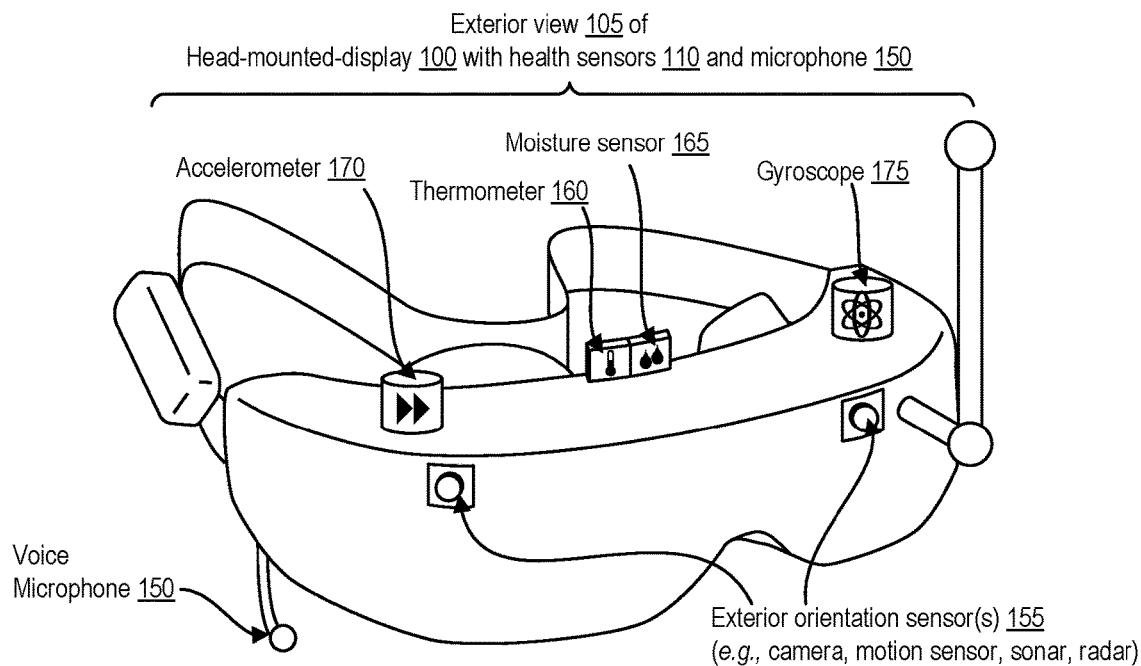
FIG. 1B illustrates an exterior view of a head-mounted display with health sensors and with a voice microphone.

FIG. 1B illustrates an exterior view 105 of a head-mounted display 100 with health sensors 110 and with a voice microphone 150.

The HMD 100 of FIG. 1B includes one or more voice microphone(s) 150, which may be used to record the voice of the user of the HMD 100 as illustrated in FIG. 4 and discussed with respect to FIG. 4. In some cases, one or more secondary microphone(s) may also be included or communicatively coupled to the HMD 100, and may be used for noise cancellation purposes. For example, a secondary microphone can be included somewhere further from the user's mouth, such as on the head strap 140 or in another device on the user's back/arm/neck/wrist/leg or in the user's hand. The audio input recorded by such a secondary microphone can be removed from the audio input recorded by the voice microphone 150 to produce "cleaned up" audio as discussed in step 410 of FIG. 4.

The HMD 100 of FIG. 1B includes various health and biometric sensors 110. For example, the HMD 100 includes one or more thermometer(s) 160, which may be used to measure the temperature of the user's body, or of the user's forehead specifically in the embodiment illustrated in FIG. 1B. In some cases, the HMD 100 may also include or be communicative coupled with a secondary thermometer further from the user's body intended to get a temperature measurement of the ambient temperature in the user's surroundings, which may be used to modify the body temperature values from the thermometer 160 to improve their accuracy. The thermometer 160 may be used to detect if a user has a fever, for example.

The HMD 100 of FIG. 1B also includes one or more moisture sensor(s) 165, which may be used to measure the moisture of the user's skin, or of the skin on the user's forehead specifically in the embodiment illustrated in FIG. 1B. This moisture sensor 165 may, for example, be a bioelectric impedance analysis (BIA) sensor or a galvanic skin response sensor. In some cases, the HMD 100 may also include or be communicatively coupled with an air humidity sensor to get ambient air humidity/moisture in the user's surroundings, which may be used to modify the moisture values from the moisture sensor 165 to improve their accuracy. The moisture sensor 165 may be used to detect if a user's sweat levels, for example.

The HMD 100 of FIG. 1B also includes one or more accelerometer(s) 170, one or more gyroscope(s) 175, and one or more exterior orientation sensor(s) 155. The exterior orientation sensor(s) 155 may include visible light cameras, infrared cameras, night vision cameras, sound navigation and ranging (SONAR) devices, radio detection and ranging (RADAR) devices, light detection and ranging (LIDAR) devices, and laser rangefinder devices. These may all be used to determine if the user is falling, moving erratically, or if the user's body position/balance/posture is poor. The HMD 100 may also be communicatively coupled to secondary accelerometer(s), gyroscope(s), or orientation sensor(s) elsewhere on the user's body to help determine the orientation and positioning of the user's body.

Figure 2A:
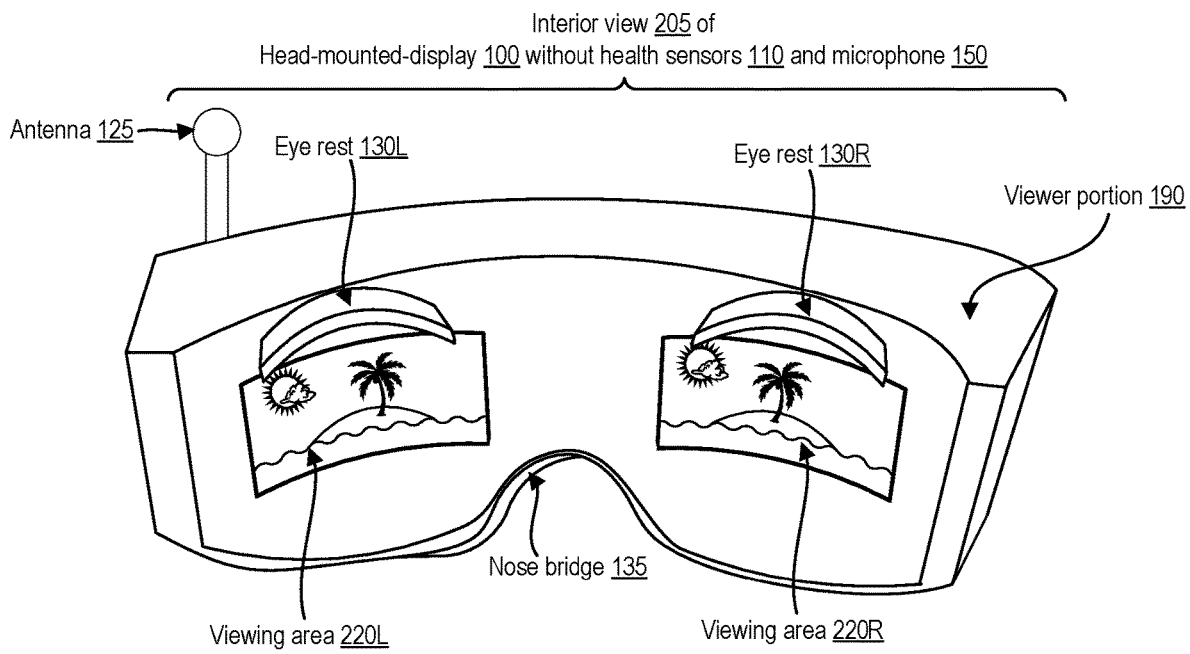
FIG. 2A illustrates an interior view of a head-mounted display without health sensors and without a voice microphone.
Figure 2B:
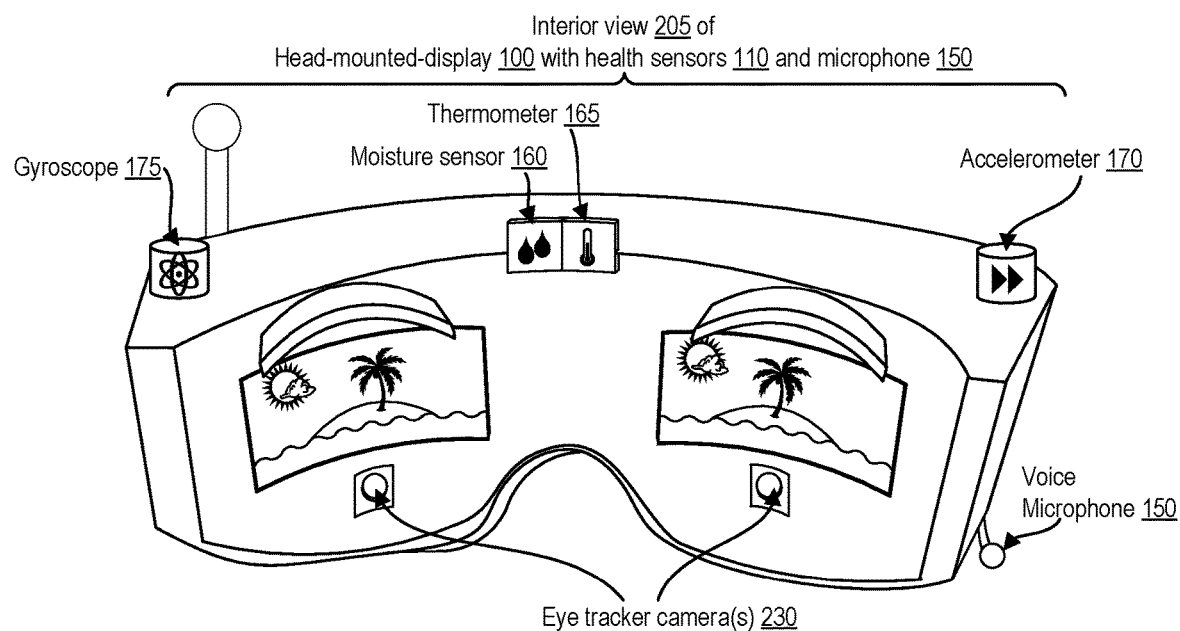
FIG. 2B illustrates an interior view of a head-mounted display with health sensors and with a voice microphone.

The HMD 100 of FIG. 1B may include, or be communicatively coupled to, any of the sensors 110 illustrated in FIG. 1B, illustrated in FIG. 2B, or mentioned in FIG. 3. The antenna 125 or another wireless communication interface of the HMD 100 may connect to various other health/biometric sensors, such as wearable devices sensors, which may include for example heart rate/pulse sensors, breathing rate sensors, blood pressure sensors, glucometer/insulin sensors, spirometers, pulsioximeters, electroencephalography (EEG) sensors, electromyography (EMG) sensor, or pressure sensor. The antenna 125 or another wireless communication interface of the HMD 100 may also connect to various environmental sensors in various "internet of things" network-connected devices such as thermostats, thermometers, humidity sensors, or air quality/allergen sensors. The antenna 125 or another wireless communication interface of the HMD 100 may also connect to various online data sources, such as online weather service websites/databases, air quality/allergen measurement websites/databases, pollution measurement websites/databases, personal workout tracking service websites/databases associated with the user, or personal diet tracking service websites/databases associated with the user. All of these data sources can be used to help adjust any health thresholds and ranges to determine if the user is suffering from a health concern, as in steps 310, 320 and 325 of FIG. 3.

FIG. 2A illustrates an interior view 205 of a head-mounted display 100 without health sensors 110 and without a voice microphone 150.

The interior view 205 of FIG. 2A illustrates the HMD 100 of FIG. 1A from a different perspective, and with the head strap 140 removed for the sake of clarity.

The HMD 100 of FIG. 2B includes two viewing areas 220 (220L and 220R), which may be individual displays or alternately may be "windows" through which a single display may be viewed by each eye of a user in either a monoscopic or stereoscopic fashion.

That is, the HMD 100 may in some cases include a single display. The single display may provide a monoscopic (two-dimensional) view, either by only displaying a single image, or by displaying the same image twice on different portions of the single display that are "cordoned off" from each other so that each eye can only see one of these portions of the display. Such "cordoning off" of different portions of a display may be accomplished via one or more opaque/reflective barriers (not shown) positioned substantially perpendicular to the display and between the display and the user. Such "cordoning off" of different portions of a display may be alternately accomplished an opaque/reflective layer positioned substantially parallel to the display and between the display and the user, with one "window" or "cutout" in the layer for each eye. The two viewing areas 220L and 220R may be such "windows" or "cutouts."

The single display may alternately provide a stereoscopic (two-dimensional) view, in which the two "cordoned off" portions of the single display show similar images, such as an identical scene but from a slightly different perspective that simulates the different perspectives of each eye caused by the distance between two eyes.

Alternately, the HMD 100 may include two separate displays—that is, each viewing area 220L and 220R may be a separate display. An HMD 100 with two displays may provide a monoscopic (two-dimensional) view by outputting the same image on both displays. An HMD 100 with two displays may alternately provide a stereoscopic (three-dimensional) view by outputting similar images on each display, such as an identical scene but from a slightly different perspective that simulates the different perspectives of each eye caused by the distance between two eyes. These two displays may be the same kind of display, or they may be different kinds of displays.

In an alternate embodiment (not pictured), the HMD 100 may replace the two viewing areas 220L and 220R with a single unified viewing area 220 having a single display.

FIG. 2B illustrates an interior view 205 of a head-mounted display 100 with health sensors 110 and with a voice microphone 150.

The interior view 205 of FIG. 2B illustrates the HMD 100 of FIG. 1B from a different perspective, and with the head strap 140 removed for the sake of clarity.

The interior view 205 of the HMD 100 of FIG. 2B illustrates that the HMD 100 includes two eye tracker cameras 230. The eye tracker cameras 230 are positioned to view the location where a user's eyes would typically be during use of the HMD 100. Each eye tracker camera 230 of FIG. 2B may be used by the HMD 100 to track a variety of eye-related parameters. For example, the eye tracker camera 230 may track blink rate, pupil dilation, eye moisture levels, eye movements, eye gaze direction, The eye tracker cameras 230 may be visible light cameras, night vision, cameras, or infrared cameras. Night vision or infrared cameras may be particularly useful if the HMD 100 is a virtual reality headset, as there may be little light in the areas that the eye tracker cameras 230 are operating.

In some cases, there may be more than one eye tracker camera 230 trained on each eye. For example, different eye tracker cameras 230 may track the user's eyes using different frequencies, such as visible light and infrared. Alternately, different eye tracker cameras 230 may track the user's eyes using different exposure lengths or using different frame rates.

In another embodiment (not shown), a single eye tracker camera 230 may be used to track both eyes. Such a single eye tracker camera 230 may either simply be spaced far enough to see both eyes, or may be positioned from an angle from which it can more easily see both eyes, such as from the side of one of the eyes, or can use additional lightguidance tools to see both eyes, such as a fish-eye lens, one or more refractive materials, one or more reflective materials, or some combination thereof.

FIG. 3 is a flow diagram illustrating a process for identifying possible concerns based on health sensor measurements.

At step 305, the HMD 100 obtains baseline measurement data 370 from a particular health/biometric sensor 360. The baseline measurement data 370 may include average data computed via means, medians, modes, or other types of averages. The baseline measurement data 370 may include several baselines value sets corresponding to times when the user was performing different activities, such as times when the user was at rest, times when the user was watching a comedy movie, times when the user was watching an action movie, times when the user was watching a scary movie, times when the user was watching a dramatic movie, times when the user was watching a movie for a short period of time, times when the user was watching a movie for a long period of time, times when the user was playing a puzzle game, times when the user was playing a racing game, times when the user was playing a first-person-shooter (FPS) game, times when the user was playing a role-playing game, times when the user was playing a strategy game, times when the user was playing a single-player game, times when the user was playing a multi-player game, times when the user was playing a game for a short period of time, times when the user was playing a game for a long period of time, or some combination thereof.

The health sensor 360 may be any one of an eye camera tracker camera 230, a external orientation sensor 155, a moisture sensor 165, a thermometer 160, an accelerometer 170, a gyroscope 175, a heart rate/pulse sensor, a blood pressure sensor, a breathing rate sensor, an air quality sensor, a glucometer/insulin sensor, a spirometer, a pulsioximeter, a electroencephalography (EEG) sensor, a voice microphone 150, a galvanic skin response sensor, an electromyography (EMG) sensor, pressure sensor, or some combination thereof.

At step 310, the HMD 100 generates a healthiness range of values 380 corresponding to a range of values that the sensor should measure under normal conditions when the user is healthy based on the baseline measurement data 370 of step 305. The healthiness range of values 380 ensures that values such as heart rate do not get too high, but also do not get too long. In some cases, only a threshold is necessary rather than a range, with the threshold being either a lower bound or an upper bound. There may be different ranges or thresholds corresponding to different user activities. For example, a first healthiness range of values 380 generated for when the user is at rest may be different than a second healthiness range of values 380 generated for when the user is playing a racing game.

Each healthiness range of values 380 or threshold may be calculated a number of ways, but may for example be calculated by adding or subtracting a predetermined multiple of a standard deviation value obtained in the baseline measurement data 370 to an average value obtained in the baseline measurement data 370. Each healthiness range of values 380 or threshold may then be tweaked by predetermined amounts based on the perceived overall health/age/weight of the user, or based on values from a different health sensor or data source other than the health sensor 306 currently being analyzed. For example, a healthiness range of values 380 corresponding to breathing rate may be narrowed if data is received indicating that air pollen/allergens are high, or may be widened if data is received indicating that air pollen/allergens are low.

At step 315, current measurement data 375 is received from the health sensor 360. At step 320, the HMD 100 identifies that the current measurement data 375 falls outside of the healthiness range of values 380 generated in step 310. In some cases, the current measurement data 375 must correspond to a number of consecutive measurements each falling outside of the healthiness range of values 380, or mostly falling outside of the healthiness range of values 380 (above a predetermined percentage). In some cases, the current measurement data 375 must correspond to consecutive measurements over a predetermined time period each falling outside of the healthiness range of values 380, or mostly falling outside of the healthiness range of values 380 (above a predetermined percentage). Such "timing" constraints ensure that outliers in the data causes by interference or sensor faultiness are not unnecessarily treated as health concerns unnecessarily. These optional "timing" constraints are illustrated in FIG. 3 as a dashed arrow going back up to step 315 from step 320.

If the current measurement data 375 is identified as falling outside of the healthiness range of values 380 at step 320, optionally with "timing" constraints as described above, then the HMD 100 identifies a possible health concern for the user at step 325.

The HMD 100 can take one or more actions as a result of the identification of the possible health concern for the user at step 325. These actions include outputting a warning to the user of the HMD 100 at step 330. The warning may be a visual warning displayed via the display(s) of the HMD 100 or an audio warning output via headphones/speakers integrated with or in communicative contact with the HMD 100. The warning may, for example, suggest that the user remove the HMD 100 for a predetermined period of time, or warn the user that the HMD 100 will be automatically turning off one or more functions after a predetermined period of time, giving the user time to properly quit or save a game.

The actions may include turning off one or more functions of the HMD 100 at step 335. This may include turning off the entire HMD 100 or putting the entire HMD 100 in a low-power "sleep" mode. Alternately, only the display may be turned off, while at least some of the health/biometric sensors may continue to operate. In some cases, if the user is playing a game, this may trigger the game to automatically pause or save, either by pausing or saving at the HMD 100 or by sending a message from the HMD 100 to a communicatively coupled video game console to force a pause, save, or game quit. If the user is playing a multiplayer game, a predetermined message may be sent to other players, allowing the user to gracefully quit the multiplayer game without angering or confusing other players.

Figure 5:
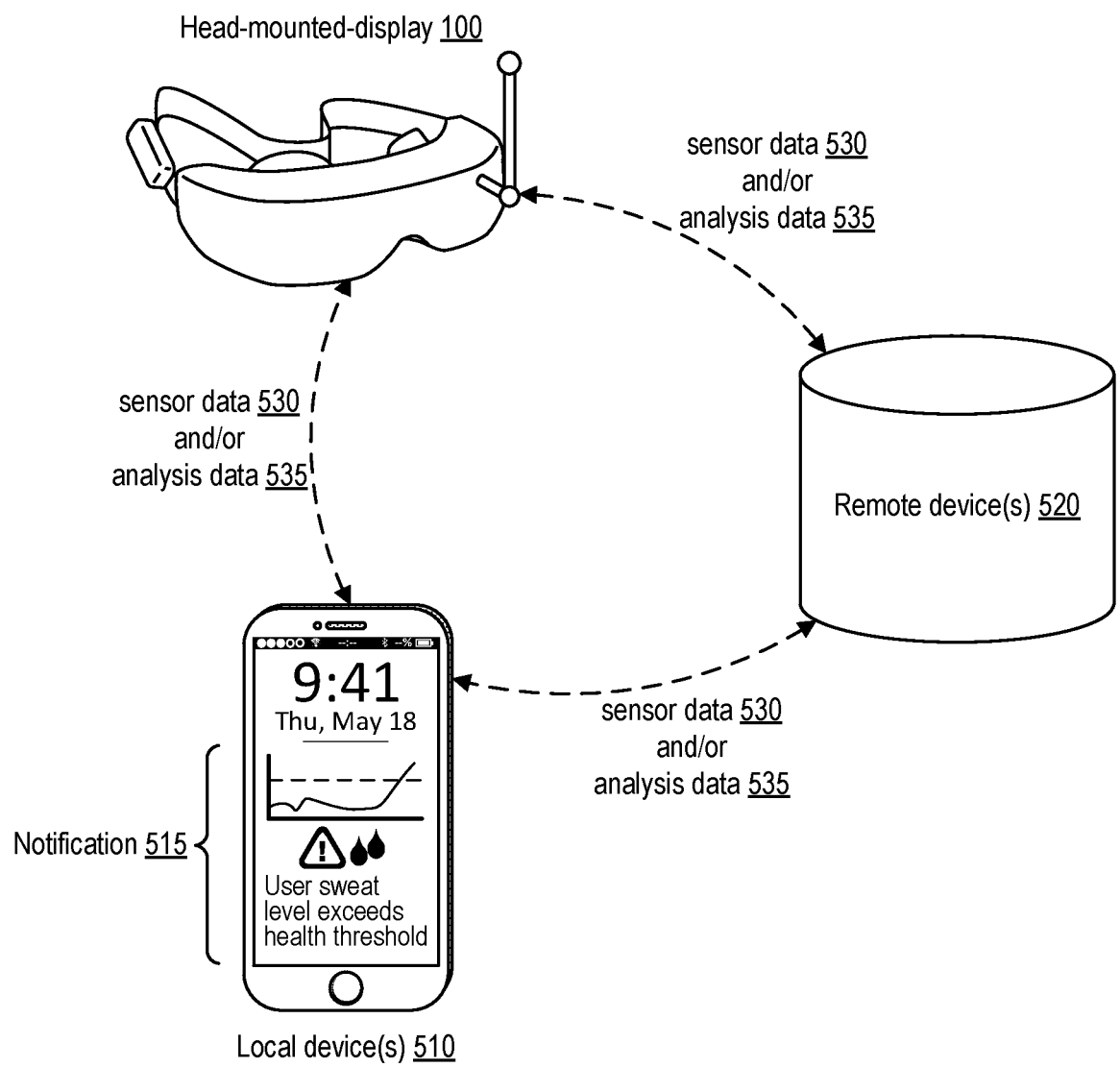
FIG. 5 illustrates a communication ecosystem that includes a head-mounted display.

The actions may include contacting an external party or device at 340. The external party/device may be one or more local device(s) 510 or remote device(s) 520. The external party/device may correspond to the user's own device, for example producing a notification 515 on the user's own phone as illustrated in FIG. 5 that they are sweating more than a healthy amount. The external party/device may correspond to a different person, such as a parent/guardian, friend, an employee, or an emergency services specialist, contacted to make sure that the user is okay and to possibly assist the user. The external party/device may correspond to an emergency services entity, such as an ambulance, a hospital, or an individual doctor/nurse, contacted to make sure that the user is okay and to assist the user. The external party/device may correspond to a content creator, such as a video game developer or filmmaker, giving the content creator feedback that the user felt sick at a particular point in the video game, movie, or other content being viewed using the HMD 100.

The actions may include triggering an alarm via an alarm system of the HMD 100 and/or an alarm system communicatively coupled to the HMD 100 at step 345. The alarm system serves to alert nearby persons that the user may need urgent assistance, and may include audio alarm indicators, such as a siren noise, and may alternately or additionally include visual alarm indicators, such as flashing lights. The alarm system may include speakers included within the HMD 100 or speakers communicatively coupled to the HMD 100, for example via a wired or wireless connection. For example, the HMD 100 may be wirelessly paired with a smartphone, and the alarm system may use the smartphone's speaker to emit an alarm sound. The alarm system may include lights or displays within the HMD 100 or lights/displays communicatively coupled to the HMD 100 to flash alarm lights. For example the HMD 100 may be wirelessly paired with an "internet of things" wirelessly-connected lightbulb directly or through an "internet of things" hub, and may trigger the "internet of things" wirelessly-connected lightbulb to flash and/or change colors.

Following the actions taken in one of steps 330, 335, 340, or 345, the process may begin again at step 305.

A number of examples are provided in FIG. 3 of current measurement data 375 falling outside of a healthiness range of values 380 as identified in step 320. These examples include identifications that: pupil dilation level is too high/low, eye moisture levels are too high/low, eye movements are erratic, eyelid blink rate is too high/low, eye gaze is are too cross-eyed/spread-out, eye squint level is too high/low, skin is too sweaty/dry, body temperature is too high/low, movement/orientation indicates user is falling, body position/posture is poor, heart rate/pulse is too high/low, blood pressure is too high/low, breathing rate is too high/low, air quality (pollen/allergens/pollution) is low, blood glucose/insulin is too high/low, breathing is too shallow/deep, blood carrying too much/little oxygen, neural activity is erratic, audible "negative phrases" (such as curse words) or "negative noises" (such as moans or snores), skin conductivity is too high/low, muscle activity abnormally high/low, the HMD 100 has been removed in the middle of an activity, the user's grip strength/pressure is too strong/weak, or some combination thereof.

FIG. 4 is a flow diagram illustrating a process for identifying possible concerns based on language processing.

At step 405, an audio input is received by the HMD 100 via the voice microphone(s) 150. At step 410, passive or active noise cancellation may optionally be used to "clean up" the audio input received in step 405, optionally using one or more secondary microphone(s) as discussed above in relation to FIG. 1B.

At step 415, speech-to-text conversion is performed on the audio input from either step 405 or step 410 in order to generate a text string. If no text is generated via the speech-to-text conversion, the HMD 100 skips to step 430; otherwise, it goes on to step 420.

At step 420, the HMD 100 compares the text string to a database of known "negative phrases," such as phrases including swear words or other known phrases suggesting discomfort, illness, or issues with the HMD 100. The database may be stored at the HMD 100 or at one or more local device(s) 510 or remote device(s) 520. This may include phrases such as "I'm feeling sick," "I want to throw up," "everything looks blurry," or "I can't see." Step 420 may optionally use "partial" or "fuzzy" matching, for example within a predetermined number of characters, to compensate for use of different verb tenses or transliteration errors made during the speech-to-text conversion. If a match is found, the HMD identifies a possible health concern at step 450.

If a match is not found at step 420, the HMD 100 may use natural language processing (NLP) techniques to identify if the text string includes language that should be classified as a "negative phrase" at step 425. For example, the HMD 100 can try tweaking verb tenses, rearranging sentences, or replacing words using a thesaurus database to see if a match would be found following such modifications to the text string. The HMD 100 can also identify dictionary definitions of individual words in the text string and use context and various artificial intelligence and machine learning techniques to infer/learn meaning and interpret if the text string includes a "negative phrase" as a result. The HMD 100 can also note use context, such as sensor data from the process described in FIG. 3, or proximity of "negative noises" in the audio input (see steps 435 and 440) to determine that a text string includes a "negative phrase." If a "negative phrase" is found, the HMD 100 identifies a possible health concern at step 450. The "negative phrase" may also be added to the database used in step 420.

In some cases, there may be no database of known "negative phrases" as described with regard to step 420, in which case step 415 may be followed immediately by step 425.

If a "negative phrase" is not found at steps 420 and 425, or if the speech-to-text transcription of step 415 produces an empty text string or no text string, the HMD 100 may, at step 430, identify and isolate portions of the audio input of step 405 or step 410 that were not converted into text during step 415, and where audio level exceed a predetermined volume level or otherwise matches some predetermined audio pattern.

At step 435, the HMD 100 compares the portions of audio isolated at step 430 to a database of known "negative noises" suggesting discomfort, illness, sleep, or issues with the HMD 100, such as sounds indicative of moans, groans, grunts, gurgles, burps, yawns, snores, screams, shrieks, yells, or gritted/gnashing teeth. This matching may use various pattern matching methods. Step 435 may optionally use "partial" or "fuzzy" matching. If a match is found, the HMD identifies a possible health concern at step 450.

If a match is not found at step 435, the HMD 100 may use machine learning or artificial intelligence techniques to try to determine if a noise should be classified as a "negative noise" at step 440. For example, the HMD 100 can analyze tones, pitches, or inflections of the noise to determine whether a noise matches tones, pitches, or inflections suggestive of discomfort, illness, sleep, or issues with the HMD 100. The HMD 100 can also note use context, such as sensor data from the process described in FIG. 3, or proximity of "negative phrases" in the audio input (see steps 420 and 425) to determine that an audio portion includes a "negative noise." If a "negative noise" is found, the HMD identifies a possible health concern at step 450. The "negative noise" may also be added to the database used in step 435.

In some cases, there may be no database of known "negative noises" as described with regard to step 435, in which case step 430 may be followed immediately by step 440.

The HMD 100 can take one or more actions as a result of the identification of the possible health concern for the user at step 450. These actions include outputting a warning to the user of the HMD 100 at step 455, as described in relation to step 330 of FIG. 3. The actions may include turning off one or more functions of the HMD 100 at step 460, as described in relation to step 335 of FIG. 3. The actions may include contacting an external party or device at 465, as described in relation to step 340 of FIG. 3. The actions may include triggering an alarm via an alarm system of the HMD 100 and/or an alarm system communicatively coupled to the HMD 100 at step 470, as described in relation to step 345 of FIG. 3.

Following the actions taken in one of steps 455, 460, 465, or 470, the process may begin again at step 405.

While the flow diagram of FIG. 4 suggests that a single negative phrase or negative noise might be reason to identify a possible concern in step 450, this need not be the case. A "negative phrase" or "negative noise" threshold similar to that of the range of step 310 of FIG. 3 might be generated and used to make this decision. For example, certain users might swear regularly in their daily routine, in which case "negative phrases" such as swearing might only be a concern if the user is using swear words at a higher rate than average during a particular time period. As such, the microphone 150 might listen to develop one or more "baseline" levels or rates of "negative phrases" or "negative noises"—for example, one while resting, one while playing racing games, one while playing first-person-shooter games, and so forth—and only identify a possible health concern at step 450 if the user's level of negative phrases exceeds the context-appropriate threshold rate for negative phrases, or if the user's level of negative noises exceeds the context-appropriate threshold rate for negative noises. That is, if the user is playing a racing game, the threshold developed based on baseline audio activity during racing games should be used, and so forth.

In some cases, the process illustrated in FIG. 4 and described herein is combined with the process illustrated in FIG. 3 and described further above. For example, a user's new measurement data 375 may fall very close to a threshold or near an edge of a healthiness range in the analysis of step 320, and a negative phrase or negative noise detected as in FIG. 4, earlier, later, or at the same time, might be used together as context to identify a possible concern. Similarly, a negative phrase or negative noise detected as in FIG. 4 but not exceeding a negativity threshold FIG. 5 illustrates a communication ecosystem that includes a head-mounted display.

The ecosystem of FIG. 5 includes a HMD 100, one or more local device(s) 510 located near the HMD 100, and one or more remote device(s) 520 located remote from the HMD 100 and the local device(s) 510. Each local device 510 and remote device 520 may include one or more computer systems 600, or may include at least a subset of any the computer system components illustrated in FIG. 6 or discussed with respect to FIG. 6.

The HMD 100 may share sensor data 530 from any of the health/biometric sensors 360, and/or analysis data 535, with local device(s) 510 and/or remote device(s) 520. Likewise, local device(s) 510 and/or remote device(s) 520 may share sensor data 530 from any of the health/biometric sensors 360, and/or analysis data 535, with each other. Analysis data 535 should be understood to refer to any analysis of sensor data 530 performed to facilitate any of the process steps illustrated in, and discussed with respect to, FIG. 3 and FIG. 4, or any intermediate/related processes/steps implied but not specifically illustrated or described therein.

Though the local device 510 of FIG. 5 is depicted as a smartphone, each local device 510 may be or include any type of computer system 600 described with respect to FIG. 6.

Though the remote device 520 of FIG. 5 is depicted as a data server, each remote device 520 may be or include any type of computer system 600 described with respect to FIG. 6.

It should be understood that any processes or steps that are described as being performed by the HMD 100 as illustrated in, and discussed with respect to, FIG. 3 and FIG. 4, can alternately or additionally be performed at the local device(s) 510 and/or the remote device(s) 520. For example, the HMD 100 may in some cases be a "dumb" device that gathers sensor data 530 and transmits it to the local device(s) 510 and/or remote device(s) 520 to be analyzed according to FIG. 3 and FIG. 4 and the corresponding descriptions herein.

Additional sensor data may be gathered using the local device(s) 510, as well—for example, one local device 510 may be a wearable device that gathers heart rate measurements from the user and sends those heart rate measurements to the HMD 100 and/or to other local device(s) 510 and/or to the remote device(s) 520. Another local device 510 may be a game controller or video remote, which may gather data about the user's grip pressure/strength and send that data to the to the HMD 100 and/or to other local device(s) 510 and/or to the remote device(s) 520.

Additional sensor data may be gathered using the remote device(s) 520, as well—for example, one remote device 520 may gather weather or air pollen/allergen information associated with the area where the user of the HMD 100 currently is and provide this information to the HMD 100 and/or to the local device(s) 510. High levels of air pollen/allergens may be cause to narrow a healthiness range in step 310 or make a threshold easier to meet/cross, and vice versa.

In some cases, the HMD 100 may only be capable of local wireless connections, such as Bluetooth connections or radio-based connections, in which case it may communicate with the remote device(s) 520 using one or more local device(s) 510, such as a smartphone, as a middleman or proxy.

FIG. 6 illustrates an exemplary computing system 600 that may be used to implement an embodiment of the present invention. For example, any of the computer systems or computerized devices described herein may, in at least some cases, include at least one computing system 600. The computing system 600 of FIG. 6 includes one or more processors 610 and memory 610. Main memory 610 stores, in part, instructions and data for execution by processor 610. Main memory 610 can store the executable code when in operation. The system 600 of FIG. 6 further includes a mass storage device 630, portable storage medium drive(s) 640, output devices 650, user input devices 660, a graphics display 670, and peripheral devices 680.

The components shown in FIG. 6 are depicted as being connected via a single bus 690. However, the components may be connected through one or more data transport means. For example, processor unit 610 and main memory 610 may be connected via a local microprocessor bus, and the mass storage device 630, peripheral device(s) 680, portable storage device 640, and display system 670 may be connected via one or more input/output (I/O) buses.

Mass storage device 630, which may be implemented with a magnetic disk drive or an optical disk drive, is a non-volatile storage device for storing data and instructions for use by processor unit 610. Mass storage device 630 can store the system software for implementing embodiments of the present invention for purposes of loading that software into main memory 610.

Portable storage device 640 operates in conjunction with a portable non-volatile storage medium, such as a floppy disk, compact disk or Digital video disc, to input and output data and code to and from the computer system 600 of FIG. 6. The system software for implementing embodiments of the present invention may be stored on such a portable medium and input to the computer system 600 via the portable storage device 640.

Input devices 660 provide a portion of a user interface. Input devices 660 may include an alpha-numeric keypad, such as a keyboard, for inputting alpha-numeric and other information, or a pointing device, such as a mouse, a trackball, stylus, or cursor direction keys. Additionally, the system 600 as shown in FIG. 6 includes output devices 650. Examples of suitable output devices include speakers, printers, network interfaces, and monitors.

Display system 670 may include a liquid crystal display (LCD), a plasma display, an organic light-emitting diode (OLED) display, an electronic ink display, a projector-based display, a holographic display, or another suitable display device. Display system 670 receives textual and graphical information, and processes the information for output to the display device. The display system 670 may include multiple-touch touchscreen input capabilities, such as capacitive touch detection, resistive touch detection, surface acoustic wave touch detection, or infrared touch detection. Such touchscreen input capabilities may or may not allow for variable pressure or force detection.

Peripherals 680 may include any type of computer support device to add additional functionality to the computer system. For example, peripheral device(s) 680 may include a modem or a router.

The components contained in the computer system 600 of FIG. 6 are those typically found in computer systems that may be suitable for use with embodiments of the present invention and are intended to represent a broad category of such computer components that are well known in the art. Thus, the computer system 600 of FIG. 6 can be a personal computer, a hand held computing device, a telephone ("smart" or otherwise), a mobile computing device, a workstation, a server (on a server rack or otherwise), a minicomputer, a mainframe computer, a tablet computing device, a wearable device (such as a watch, a ring, a pair of glasses, or another type of jewelry/clothing/accessory), a video game console (portable or otherwise), an e-book reader, a media player device (portable or otherwise), a vehicle-based computer, some combination thereof, or any other computing device. The computer system 600 may in some cases be a virtual computer system executed by another computer system. The computer can also include different bus configurations, networked platforms, multi-processor platforms, etc. Various operating systems can be used including Unix, Linux, Windows, Macintosh OS, Palm OS, Android, iOS, and other suitable operating systems.

In some cases, the computer system 600 may be part of a multi-computer system that uses multiple computer systems 600, each for one or more specific tasks or purposes. For example, the multi-computer system may include multiple computer systems 600 communicatively coupled together via at least one of a personal area network (PAN), a local area network (LAN), a wireless local area network (WLAN), a municipal area network (MAN), a wide area network (WAN), or some combination thereof. The multi-computer system may further include multiple computer systems 600 from different networks communicatively coupled together via the internet (also known as a "distributed" system).

The present invention may be implemented in an application that may be operable using a variety of devices. Non-transitory computer-readable storage media refer to any medium or media that participate in providing instructions to a central processing unit (CPU) for execution, and that may be used in the memory 620, the mass storage 630, the portable storage 640, or some combination thereof. Such media can take many forms, including, but not limited to, non-volatile and volatile media such as optical or magnetic disks and dynamic memory, respectively. Some forms of non-transitory computer-readable media include, for example, a floppy disk, a flexible disk, a hard disk, magnetic tape, any other magnetic medium, flash memory, memristor memory, any other solid-state memory, a CD-ROM disk, digital video disk (DVD), blu-ray disk (BDD), or any other optical medium, Random Access Memory (RAM), Read-Only Memory (ROM), programmable read-only memory (PROM), erasable programmable read-only memory (EPROM), electrically erasable programmable read-only memory (EEPROM), FLASHEPROM, Resistive random-access memory (RRAM or ReRAM), Phase Change Memory (PCM), spin transfer torque RAM (STT-RAM), and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

While various flow diagrams provided and described above may show a particular order of operations performed by certain embodiments of the invention, it should be understood that such order is exemplary. Alternative embodiments may perform the operations in a different order, combine certain operations, overlap certain operations, or some combination thereof.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for illness mitigation during gameplay involving use of a head-mounted display (HMD), the method comprising:
    receiving one or more baseline sensor measurement values from a health sensor under conditions designated as normal, the baseline sensor measurement values measuring a health characteristic of a user of the head-mounted display (HMD) during gameplay of a plurality of different types of games;
    generating a health threshold value set based on the baseline sensor measurement values for the different types of games, wherein each different type of game is associated with a different health threshold value in the health threshold value set;

receiving game data indicating that the user is playing a game at an identified time period;

receiving an active sensor measurement value from the health sensor during gameplay of the game at the identified time period, wherein the active sensor measurement value measures the health characteristic of the user of the head-mounted display (HMD) following generation of the health threshold value;

identifying a type of the game being played at the identified time period indicated by the game data;

identifying which of the different health threshold values in the health threshold value set is associated with the identified type of the game;

identifying that the active sensor measurement value has reached or crossed the identified health threshold value associated with the identified type of the game; and displaying a visual indicator on a display portion of the head-mounted display (HMD) in response to the identification that the active sensor measurement value has reached or crossed the identified health threshold value associated with the identified type of the game.

2. The method of claim 1, further comprising activating an audio output device associated with the head-mounted display (HMD) to play an audible warning in response to the identification that the active sensor measurement value has reached or crossed the identified health threshold value.

3. The method of claim 1, further comprising turning off one or more functions of the head-mounted display (HMD) in response to the identification that the active sensor measurement value has reached or crossed the identified health threshold value.

4. The method of claim 1, further comprising sending a transmission to an external device in response to the identification of the health concern, wherein the transmission includes at least one of a text-based notification, an audio-based notification, or a visual notification.

5. The method of claim 1, wherein the health sensor is a thermometer, and wherein the active sensor measurement value is a body temperature measurement value of the user of the head-mounted display (HMD).

6. The method of claim 1, wherein the health sensor is at least one of a moisture sensor or a galvanic skin response sensor, and wherein the active sensor measurement value is a skin sweat measurement value of the user of the head-mounted display (HMD).

7. The method of claim 1, wherein the health sensor is a camera, and wherein the active sensor measurement value concerns at least one eye of the user of the head-mounted display (HMD), and wherein the active sensor measurement value is at least one of a pupil dilation measurement value, an eye movement measurement value, or an eye moisture measurement.

8. The method of claim 1, wherein the health sensor is at least one of a accelerometer or a gyroscope, and wherein the active sensor measurement value concerns at least one of an orientation or a position of the user of the head-mounted display (HMD).

9. The method of claim 1, wherein the health sensor is a microphone, and wherein the active sensor measurement value corresponds to an attribute of a noise made by the user of the head-mounted display (HMD).

10. The method of claim 1, wherein identifying that the active sensor measurement value has reached or crossed the health threshold value includes identifying that the active sensor measurement value has reached or exceeded the health threshold value.

11. The method of claim 1, wherein identifying that the active sensor measurement value has reached or crossed the health threshold value includes identifying that the active sensor measurement value has reached or fallen below the health threshold value.

12. The method of claim 1 further comprising:

receiving new game data that includes a new active sensor measurement value during gameplay of a different game;

identifying that the new game data was obtained from a type of the different game, the identified type of the different game being different from the identified type of the game;

identifying which of the different health threshold values in the health threshold value set is associated with the different type of the different game;

identifying that the new active sensor measurement value has reached or crossed the health threshold value identified as associated with the different type of the different game; and generating a notification on a display device associated with the HMD.

13. A head-mounted display (HMD) system for illness mitigation, the head-mounted display (HMD) system comprising:

a body to be worn on a head of a user;

a display integrated with the body;

a memory to store instructions;

a health sensor that provides one or more baseline sensor measurement values under conditions designated as normal, the baseline sensor measurement values measuring a health characteristic of the user during gameplay of a plurality of different types of games, a processor coupled to the memory, wherein execution of the instructions by the processor causes the head-mounted display (HMD) system to:

generate a health threshold value set based on the baseline sensor measurement values for the different types of games, wherein each different type of game is associated with a different health threshold value in the health threshold value set, receives game data indicating that the user is playing a game at an identified time period, receive an active sensor measurement value from the health sensor during gameplay of the game at the identified time period, wherein the active sensor measurement value measures the health characteristic of the user of the head-mounted display (HMD) following generation of the health threshold value, identify a type of the game being played at the identified time period indicated by the game data, identify which of the different health threshold values in the health threshold value set is associated with the identified type of the game;

identify that the active sensor measurement value has reached or crossed the identified health threshold value associated with the identified type of the game, and display a visual indicator on the display integrated with the body in response to the identification that the active sensor measurement value has reached or crossed the identified health threshold value associated with the identified type of the game.

14. The head-mounted display (HMD) system of claim 13, further comprising a wireless communication interface, wherein the head-mounted display (HMD) system receives the baseline sensor measurement value and the active sensor measurement value from the health sensor wirelessly via the wireless communication interface.

15. The head-mounted display (HMD) system of claim 13, further comprising an alarm system that includes at least one of an audio output device or a visual output device, wherein execution of the instructions by the processor causes the head-mounted display (HMD) system to activate the alarm system in response to the identification that the active sensor measurement value has reached or crossed the identified health threshold value.

16. The head-mounted display (HMD) system of claim 15, wherein the alarm system outputs:
an audible warning output via the audio output device associated with the head-mounted display (HMD) system, or
a visual warning output via the visual output device on the display of the head-mounted display (HMD) system.

17. The head-mounted display (HMD) system of claim 13, further comprising a wireless communication interface, wherein execution of the instructions by the processor causes the head-mounted display (HMD) system to send a transmission to an external device via the wireless communication interface in response to the identification of the health concern, wherein the transmission includes at least one of a text-based notification, an audio-based notification, or a visual notification.

18. A non-transitory computer readable storage medium having embodied thereon a program, wherein the program is executable by a processor to perform a method of illness mitigation during gameplay involving use of a head-mounted display (HMD), the method comprising:

receiving one or more baseline sensor measurement values from a health sensor under conditions designated as normal, the baseline sensor measurement values measuring a health characteristic of a user of the head-mounted display (HMD) during gameplay of a plurality of different types of games;

generating a health threshold value set based on the baseline sensor measurement values for the different types of games, wherein each different type of game is associated with a different health threshold value in the health threshold value set;

receiving game data indicating that the user is playing a game at an identified time period;

receiving an active sensor measurement value from the health sensor during gameplay of the game at the identified time period, wherein the active sensor measurement value measures the health characteristic of the user of the head-mounted display (HMD) following generation of the health threshold value;

identifying a type of the game being played at the identified time period indicated by the game data;

identifying which of the different health threshold values in the health threshold value set is associated with the identified type of the game;

identifying that the active sensor measurement value has reached or crossed the identified health threshold value associated with the identified type of the game; and displaying a visual indicator on a display portion of the head-mounted display (HMD) in response to the identification that the active sensor measurement value has reached or crossed the identified health threshold value associated with the identified type of the game.

\* \* \* \* \*